United States Patent
Steer (10) Patent No.: US 6,656,169 B1
(45) Date of Patent: Dec. 2, 2003

(54) OSTOMY OR INCONTINENCE POUCH (75) Inventor: Graham L. Steer, London (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/468,397

(22) Filed: Dec. 20, 1999

(30) Foreign Application Priority Data

Dec. 23, 1998 (GB) ............................................. 9828626
Mar. 2, 1999 (GB) ............................................. 9904775

(51) Int. Cl.7 ................................................. A61F 5/44
(52) U.S. Cl. ..................................................... 604/333
(58) Field of Search ............................... 604/327, 331, 604/332, 333

(56) References Cited

U.S. PATENT DOCUMENTS 5,860,959 A * 1/1999 Gent ........................... 604/332
6,129,716 A * 10/2000 Steer ........................... 604/333

* cited by examiner

Primary Examiner—Weilun Lo
Assistant Examiner—Michael G. Bogart
(74) Attorney, Agent, or Firm—Stuart E. Krieger (57) ABSTRACT An ostomy pouch (10) is defined by a front wall (12) and a rear wall (14) having a stoma aperture (18). One or more rupturable capsules (24) are carried on a carrier or intervening wall (44) welded to the front and rear walls at a common weld seam (16). When desired, a capsule (24) can be ruptured by squeezing, the pouch wall together at that position, to dispense the contents (for example, a deodorising agent, a disinfectant or a preservative). In one form, the carrier does not cover the stoma aperture. In another form, the contents are dispensed on the side facing the front wall (12), and the curtain (44) shields the stoma aperture (18), to prevent the agent spurting out or contacting the stoma. In another form, one or more rupturable capsules may be arranged on the front wall (12) or on the rear wall (14). A plurality of the capsules (24) may contain different agents if desired. In another form, one or more self-dissolving capsules, for example, of gelatine, may be introduced into the pouch to dispense the agent in response to environmental conditions (for example, temperature/humidity) within the pouch.

30 Claims, 10 Drawing Sheets

OSTOMY OR INCONTINENCE POUCH

This invention relates to an ostomy or incontinence pouch containing a pocket or capsule for release of an agent for affecting the contents of the pouch. For example, the agent may be a malodour counteractant for countering unpleasant odours (by chemical reaction, absorption or masking), or a disinfectant for reducing the harmfulness of the contents, or a preservative for slowing decomposition of the contents.

An ostomy pouch using rupturable container bubbles is known, for example, from U.S. Pat. No. 5,411,496. The bubbles contain a deodorising agent which is released by application of external pressure to rupture a bubble. The bubbles are attached to a carrier which is secured to the interior face of the front or rear wall of the pouch at the bottom of the pouch. However, the specification does not explain how the bubbles are attached, in practice, to the pouch walls.

A urine pouch using rupturable containers is known, for example, from U.S. Pat. No. 4,461,100. The containers contain disinfectant, and rupture in response to the application of external pressure. In one form, the containers are included within a seam of the pouch. Such a construction requires careful handling during manufacture, to ensure that a good seal is obtained in the seam around the containers, but without risking accidental pressure rupture of any containers. Such rupture would prevent the seam from being welded properly, and could also interfere with the welding machinery which would then have to be stopped and cleaned. In other forms, the containers are placed loose, or in a loose strip, within the pouch. However, such loose squeezable containers are not preferred by customers, since it can be difficult to find a mobile unruptured container simply by feel, and it may be difficult to hold a container stationary while applying sufficient pressure to rupture the container.

The present invention has been devised bearing the above problems in mind.

BRIEF SUMMARY OF THE INVENTION

In contrast to the prior art, one aspect of the present invention is to provide at least one capsule containing an agent for affecting the pouch contents, the capsule releasing the agent when the capsule is affected by environmental conditions within the pouch. For example, the capsule may be responsive to temperature and/or humidity conditions.

With the above technique, the capsule does not have to be ruptured by application of external pressure. Instead, the capsule can release the agent automatically in response to conditions within the pouch when the pouch is used. Such a capsule can provide a method of automatically releasing the agent into the pouch with very little manual intervention.

When the pouch is worn on the body, the temperature and humidity within the pouch typically increase, providing a warm, humid environment which can be used to trigger release of the agent.

The material may be of a type which dissolves, or thins, or becomes permeable to some extent, in the presence of elevated temperature and/or humidity conditions. Additionally, the capsule may have a construction which is responsive to the humidity and/or temperature conditions. For example, the capsule may consist of a plurality of shell parts which separate or become leaky at the joint between the shell parts.

The material may, for example, comprise gelatine. Additionally, or alternatively, the material may comprise a synthetic material. A capsule can be provided which is stable in relatively dry conditions at room temperature, but which releases the agent when subjected to the temperature and humidity conditions normally found in an ostomy or incontinence pouch when in use.

Preferably, the agent is in liquid form. This can provide good dispersion of the agent within the pouch when the agent is released from the capsule.

Preferably, the agent is water based. For example, the agent may consist of an aqueous solution of a malodour counteractant. For example, the malodour counteractant may be an oxidising agent, such as hydrogen peroxide.

The capsule may be loose in the pouch, or it may be secured or captively mounted within the pouch. If a loose capsule is used, then this might be introduced into the pouch by the user prior to fitting the pouch. Such a technique can avoid the potential manufacturing problems associated with producing pouches with one or more capsules installed within the pouch.

It will be appreciated that a loose capsule in accordance with the above aspect of the invention does not suffer from the drawbacks associated with the squeezable capsules of the prior art because the user does not have to locate, and squeeze, the capsule through the pouch wall.

In a closely related aspect, the invention provides a capsule introducable into an ostomy or incontinence pouch, the capsule containing an agent for affecting the contents of the pouch, the capsule comprising a material able to release the agent in response to temperature and/or humidity conditions.

A further aspect of the present invention is to mount one or more pockets (also referred to herein as "bubbles" or "capsules") on or in a wall or wall segment positioned between the front and rear walls of the pouch, and attached to both the front and rear walls at a common weld seam between the front and rear walls, the pockets being clear of the weld seam.

This aspect can be used with the self-activating capsules of the first aspect, or with rupturable pockets which, in use, are squeezed by the user to cause the pocket to rupture and to release the agent into the pouch.

Such a construction can permit the pockets or capsules to be fixed in position relative to the front and rear walls, without risking accidental rupture of the pockets during welding, and without compromising the seal strength of the seam. Furthermore, the wall carrying the pockets or capsules can be welded during the same welding operation for securing the front and rear walls together. Therefore, no additional welding steps are required.

Another closely related aspect is to provide, in an ostomy or incontinence pouch, an internal wall to shield, at least to some extent, the stoma or entrance aperture from direct contact with the agent released from a pocket or capsule during release.

For example, the wall may be a curtain which extends over the aperture. Additionally, or alternatively, the wall may be a curtain which extends over the pocket or capsule.

The agent contained in the pocket or capsule will normally be in concentrate form, and it can be highly undesirable for the concentrate to directly contact the ostomate's sensitive stoma. For example, the concentrate may cause very unpleasant irritation of the stoma.

With a shielding wall as defined above, the sensitive stoma can be protected. This can allow even stronger concentrates of agents to be used. It will be appreciated that, once the agent has dispersed into the pouch, there is less risk of stoma irritation. Nevertheless, the shielding wall can provide excellent protection during initial release of the agent when the concentration is at its strongest.

It will be appreciated that the ostomate may rupture a rupturable pocket either before fitting the pouch, or after fitting the pouch. In the former case, the shielding wall provides a further advantage in preventing the agent from accidentally spurting out through the stoma aperture as the pocket is "popped" open. Such spurting is highly undesirable, as it may result in the agent landing on the ostomate's skin, or clothes. For example, if the agent is a concentrated deodorising agent, it may have a very pungent odour which would be difficult to wash away from clothes or from the skin, and would be very embarrassing.

The use of a shielding wall can also allow the safe use of a pocket or capsule on or in a wall of an ostomy pouch and clear of a peripheral seam of the pouch, the pocket or capsule being positioned closer to the pouch stoma aperture than to the lowermost point of the pouch when in its normal orientation.

Such an arrangement can provide two advantages. Firstly, the elevation of the pocket(s) or capsules can provide better dispersal of the agent as the agent is released into the pouch. Secondly, if additional agent needs to be released part way through use of the pouch, the agent can be released on to, or into, the newest contents of the pouch, for which the additional agent will be intended.

The wall carrying the pocket or capsule may be an interior wall, or an exterior wall. In the latter case, the pocket or capsule is engineered to rupture on or through the interior face of the wall, so that the contents are released internally in the pouch.

Another closely related aspect of the invention is to provide at least one pocket or capsule on or in the wall of the pouch which also has a stoma aperture, the pocket or capsule being configure to rupture on, or through, the wall into the interior of the pouch.

Preferably, the pocket or capsule is located at a position closer to the stoma aperture than to the lower most region of the pouch when in its normal orientation.

Another closely related aspect of the invention is to provide a plurality of pockets or capsules, in which first and second pockets/capsules contain non-identical agents for affecting the contents of the pouch in different ways and/or to different extents.

For example, the different agents may be intended for use at different times, perhaps one being for use prior to fitting the pouch, (for example, a deodorant and a disinfectant), and the other being for use prior to removing the pouch for disposal (for example, a strong deodorant).

Although the above aspects provide advantages when used independently, further advantages are provided by using two or ore of the aspects in combination.

Embodiments of the invention are now described, by way of example only, with reference to the accompanying drawings, in which.

Figure 19:
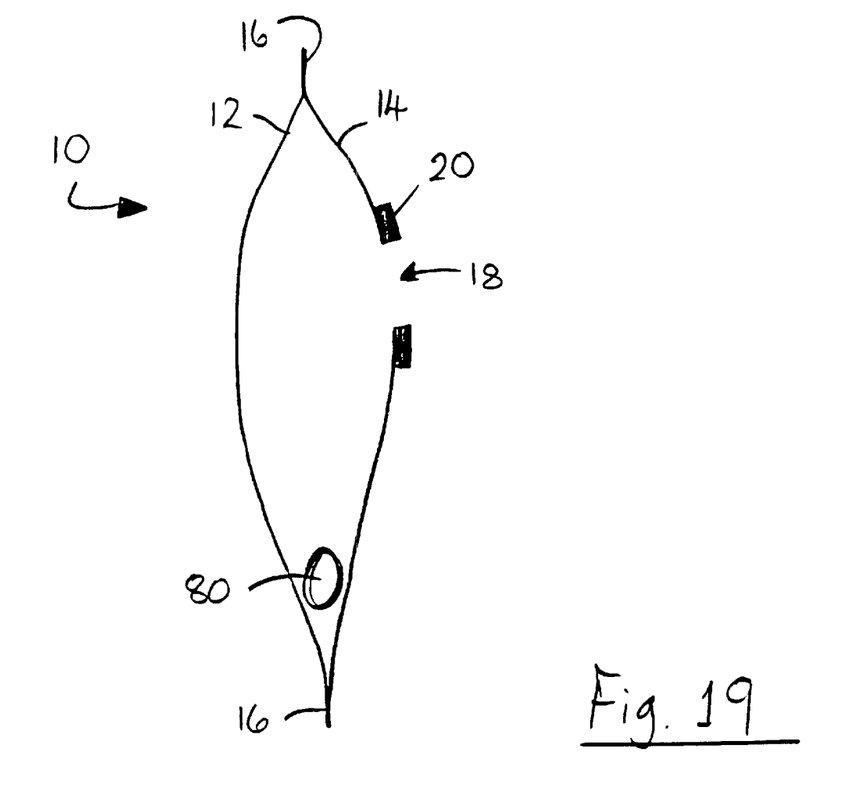
FIG. 19 is a schematic section through an ostomy pouch containing a loose capsule.

Referring firstly to FIG. 19, an ostomy pouch 10 is defined by a front wall 12 and a rear wall 14 welded together at a seam 16 around their peripheral edges. The walls are made of plastics film, which may include a barrier layer to prevent or reduce odour transpiration through the wall material. A suitable film is, for example, MF film available from Cryo Vac (Sealed Air Corporation).

The rear wall 14 is formed with a stoma aperture 18, surrounded by a coupling ring 20 welded to the rear wall 14. The coupling ring 14 enables the pouch to be coupled to the ostomate's peristomal region. In the illustrated form, the coupling ring 18 is of a type which forms a mechanical coupling with a complementary bodyside coupling part (not shown) worn by the ostomate. Such arrangements are well known, particularly effective designs being illustrated for example in EP-A-0737456, EP-A-0737457, EP-A-0737458, EP-A-0737459 and EP-A-0737460. In an alternative form, the coupling ring 20 may be a conventional adhesive wafer for attachment directly to the ostomate's skin.

A capsule 80 is loosely received within the pouch 10. The capsule may either be introduced by the user through the stoma aperture 18 prior to wearing the pouch, or the capsule may be pre-installed within the pouch 10 during production of the pouch.

Figure 20:
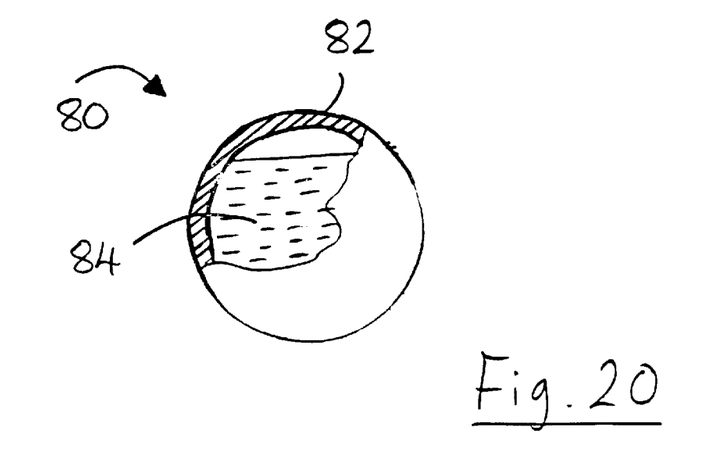
FIG. 20 is a schematic cutaway section through a capsule used in FIG. 19.

Referring to FIG. 20, the capsule 80 comprises a shell 82 containing, in this embodiment, a liquid agent 84 for affecting the pouch contents. For example, the agent may be a malodour counteractant, such as an oxidising agent (e.g. hydrogen peroxide).

The shell 82 is made of a material, or has a particular construction, to enable the shell automatically to release the agent 84 in response to environmental conditions within the pouch 10. For example, the shell 82 may rupture, or split apart, or dissolve, or become at least partly permeable, in response to temperature and/or to humidity conditions.

In this embodiment, the shell 82 comprises gelatine, or a synthetic material. The shell 82 is stable under dry conditions at room temperature, but releases the agent 84 when subjected to the relatively high humidity within an ostomy pouch when worn, and/or when subjected to the relative warmth within an ostomy pouch when worn. This can enable a capsule to be provided which can be handled relatively safely by the user to insert the capsule into the pouch, but which releases the agent automatically when the pouch is subsequently worn.

The capsule 80 may release the agent 84 in a burst, or it may release the agent progressively over time.

It is preferred in this embodiment that the agent 84 be water based (for example an aqueous solution of hydrogen peroxide), and that the shell 82 be able to contain the water based agent without prematurely dissolving or rupturing.

The following embodiments concentrate on mounting rupturable pockets or bubbles within pouch constructions. However, it will be appreciated that the same principles may be applied to mount a capsule 80 in the same manner if desired, and the following embodiments are intended to be read with such an understanding.

Figure 1:
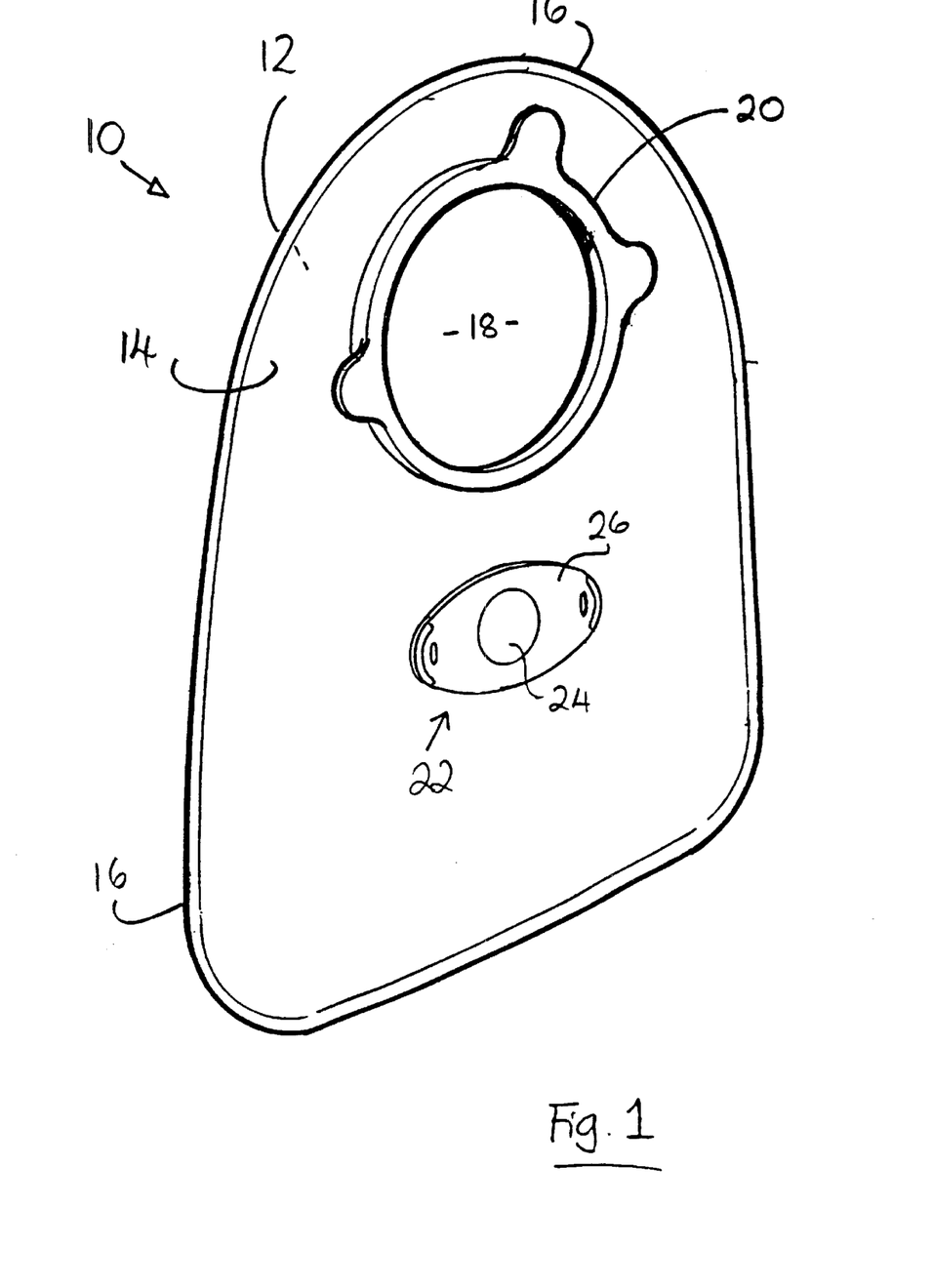
FIG. 1 is a schematic perspective view of an ostomy pouch using the invention.
Figure 2:
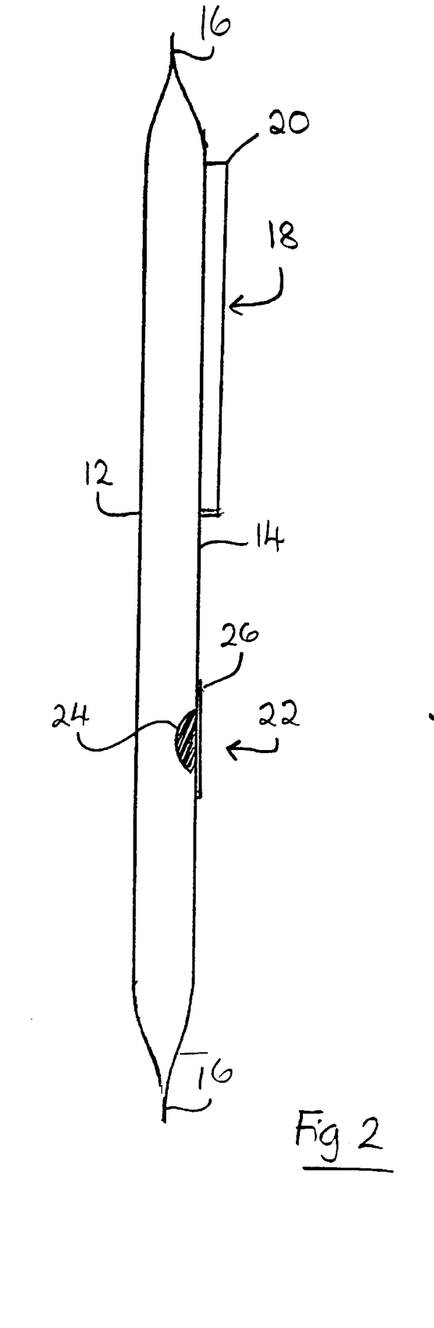
FIG. 2 is a sectional view of the pouch of FIG. 1.
Figure 3:
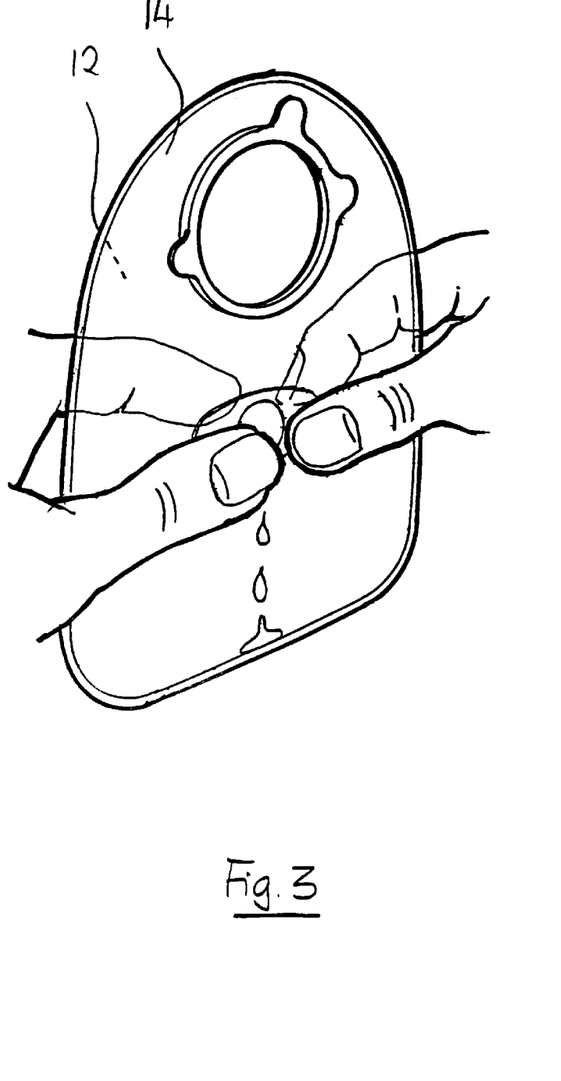
FIG. 3 is a schematic perspective view illustrating rupturing of the pocket.

Referring to FIGS. 1–3 (the same reference numerals as above being used where appropriate), an ostomy pouch 10 is illustrated with a rupturable capsule 22 mounted on the rear wall 14. The rupturable capsule 22 includes a rupturable pocket 24 containing an additive, or agent, to be dispensed into the pouch interior. The additive (or agent) may, for example, be a deodorising agent for absorbing or masking unpleasant odours, or a disinfectant for reducing the harmfulness of the contents, or a preservative for slowing decomposition of the contents, or a combination of any of the foregoing.

In the illustrated embodiment, the capsule 22 is mounted on the exterior face of the rear wall 14, with the rupturable pocket 24 projecting through an opening in the rear wall 14. The capsule 22 is secured in position by welding a flange 26 surrounding the rupturable pocket 24. Referring to FIG. 3, in use, the agent is dispensed into the pouch interior by squeezing together the front wall 12 and the rear wall 14 of the pouch in the vacinity of the capsule 22. This ruptures the pocket 24, allowing the agents to be released into the pouch interior. In the illustrated embodiment, the capsule 22 is located at a position elevated above the lower most region of the pouch to enable the agent to be dispersed more effectively within the pouch interior. If desired, the position of the capsule 22 could be raised even further, so that it is even closer to the stoma aperture 18.

By positioning the capsule 22 on the rear wall 14, there is a much smaller risk of the agent sparting out through the stoma aperture 18 than if the capsule were to be mounted on the front wall 12. It will be appreciated that, if the capsule 22 is ruptured prior to fitting the pouch, any agent which spurts out through the stoma aperture 18 could land on the ostomate's hands or clothes. Since the agent is normally in concentrate form, this could lead to skin irritation, or pungent odours which would be difficult to remove. Also, if the capsule 22 is ruptured while the pouch 10 is being worn, any agent spurting through the stoma aperture 18 could irritate the wearer's stoma, which would be very uncomfortable.

Figure 4:
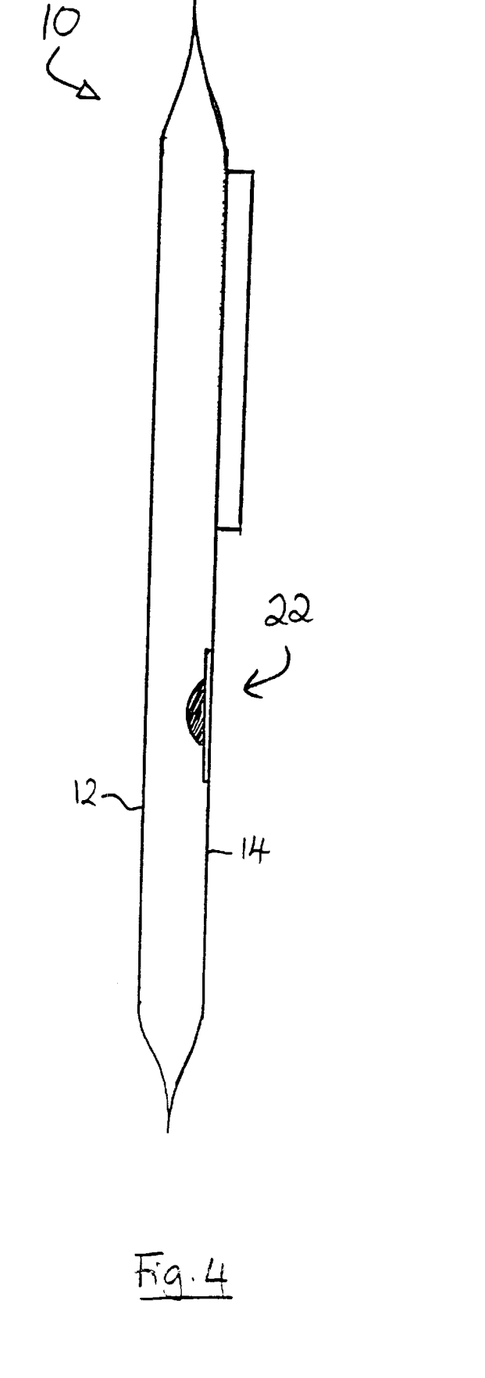
FIG. 4 is a sectional view of a second embodiment of ostomy pouch.

FIG. 4 illustrates a modified construction of the pouch 10 using the capsule 22. In this modified embodiment, the capsule 22 is mounted in the interior face of the rear wall 14, rather than on the exterior face. This can avoid the need to have to form and seal around, an opening in the rear wall 14 to accommodate the capsule 22. If will be appreciated that the capsule 22 dashed of FIG. 3 is ruptured in exactly the same way as that illustrated in FIG. 2.

Figure 5:
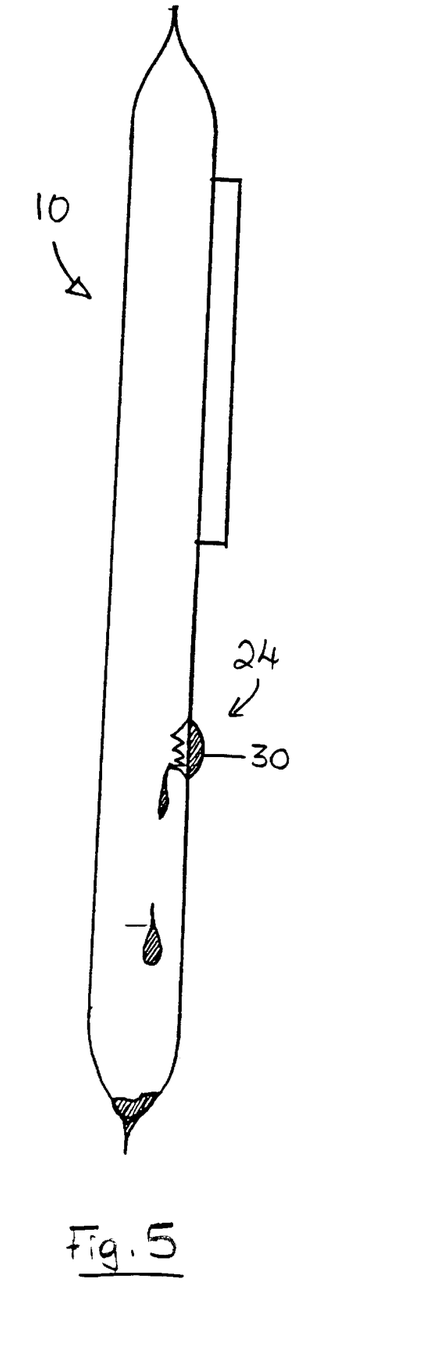
FIG. 5 is a sectional view through third embodiment of pouch.

FIG. 5 illustrates a further modified construction in which the rupturable pocket 24 is formed as an integral bubble 30 in the plastics film forming the rear wall of the pouch. This can avoid the need to have to weld a separate capsule 22 in place. However, depending on the construction of the plastic film, it might be more expensive to produce an integral bubble 24 and so, at present, this construction is less preferred.

Figure 6:
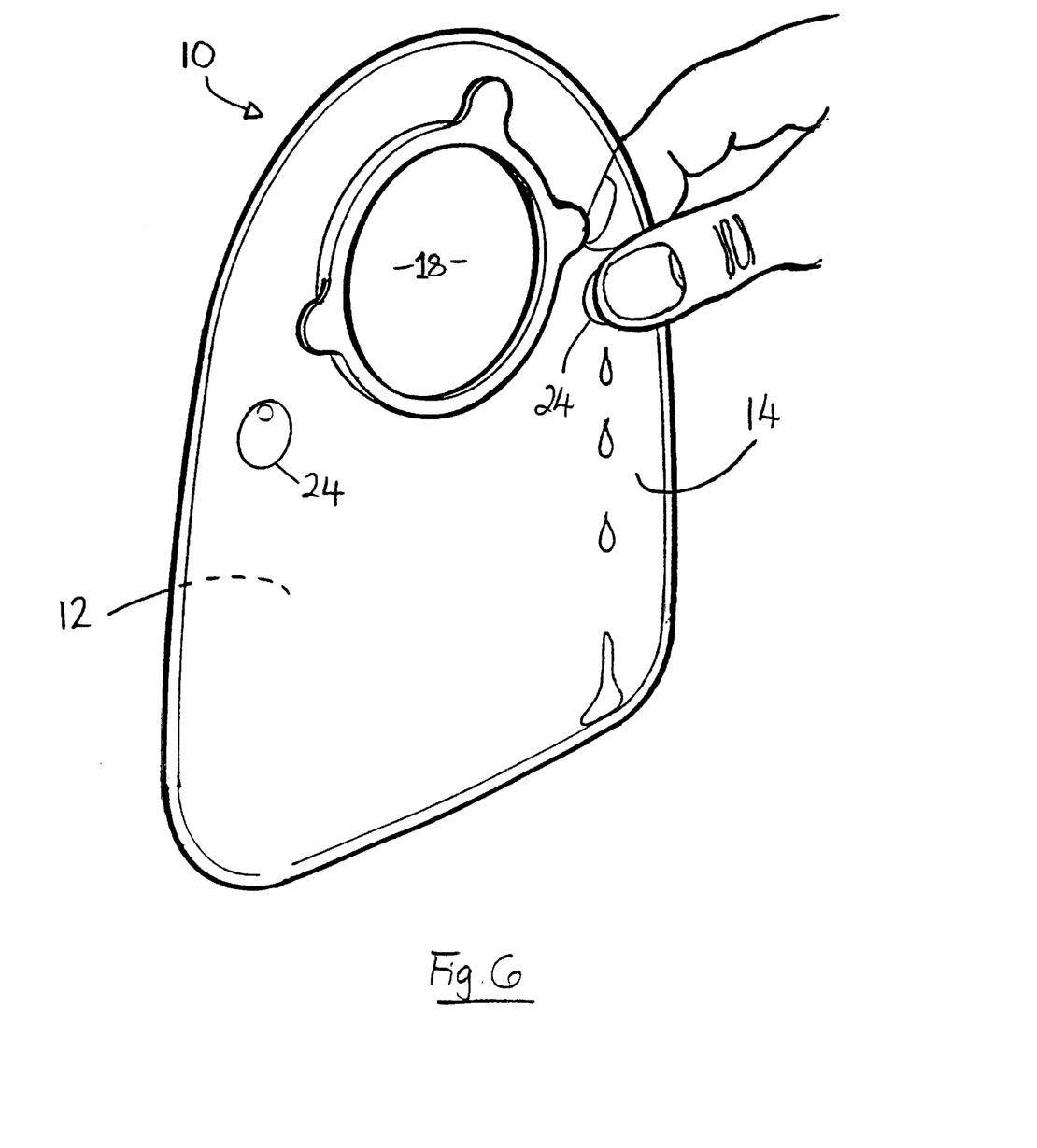
FIG. 6 is a schematic perspective view of a fourth alternative embodiment.

FIG. 6 illustrates a further embodiment which includes a plurality (two) rupturable pockets 24. The pockets are provided at elevated positions on the rear wall 14 on either side of the stoma aperture 18. The provision of a plurality of pockets 24 can provide the ostomate with greater versatility in deciding when to release the agent, and how much agent needs to be used. For example, the ostomate might decide to rupture one of the pockets 24 to release the agent just prior to, or just after, fitting the pouch. The other pocket 24 could be ruptured just prior to removal of the pouch for disposal. This could be particularly advantageous if the pockets 24 contain a deodorising agent, so that the pouch contents can be deodorised while the pouch is being worn and also extra deodorant can be dispensed just prior to removal to reduce the chances of unpleasant odours emanating from the pouch when the stoma aperture 18 is exposed.

A further feature of providing more than one rupturable pocket 24 is that different pockets may contain different additives or agents, if desired. For example, one of the pockets could contain a mixture of a deodorising agent and a disinfectant (for early release into the pouch), and a second pocket could contain simply a deodorising agent (for release into the pouch shortly prior to removal). If desired, the rupturable pockets could be colour coded to indicate the contents of each rupturable pocket.

Figure 7:
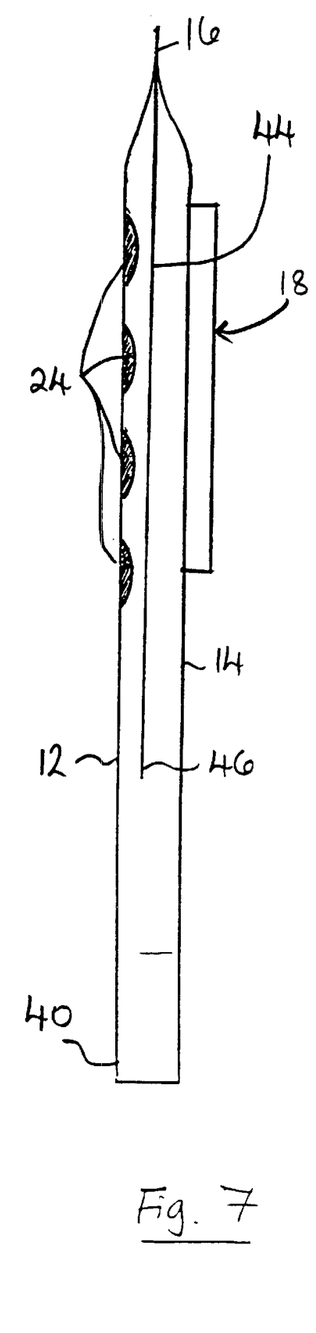
FIG. 7 is a sectional view through a fifth ileostomy pouch.

FIG. 7 illustrates a further embodiment of ostomy pouch in which one or more rupturable pockets 24 are mounted on a carrier wall or curtain 32. In this embodiment, the curtain is joined to the front and rear walls 12 and 14 at the common weld seam 16, and depends therefrom. The curtain 32 extends partly around the stoma aperture 18 and has a curved shape so as not to obstruct the aperture.

FIG. 7 illustrates a further embodiment of ostomy pouch, in particular, an ileostomy pouch having an open chute 40 at its lower most point. In use, the chute is normally folded on itself and clamped closed by means of a clip (e.g. 42 in FIG. 8). In the pouch illustrated in FIG. 7, a plurality of rupturable pockets 24 are provided on the front wall 12, instead of on the rear wall 14. The pockets 24 are shielded from the ostomy aperture 18 by means of an intervening curtain 44 of flexible plastic material (for example, the same plastics material as the front wall 12 and rear wall 14). In the present embodiment, the curtain 44 is joined to both the front wall 12 and the rear wall 14 at the common weld seam 16. Therefore, the curtain 44 is secured at its uppermost region, and also along its sides. However, the lower edge 46 of the curtain 44 hangs free so that the curtain 44 will not substantially obstruct entry of stomal discharge into the pouch. It will be appreciated that, in other embodiments, the curtain 44 may be attached or suspended differently provided that the curtain is able to shield the stomal aperture 18 to prevent (at least to a significant extent) agent or additive released from a rupturable pocket 24 from spurting directly through the aperture 18.

The rupturable pockets 24 are arranged in one or more generally upright arrangements. The pockets are offset laterally from the stoma aperture 18 to enable the pockets to be ruptured by squeezing together the front and rear walls of the pouch at an appropriate position.

Figure 8:
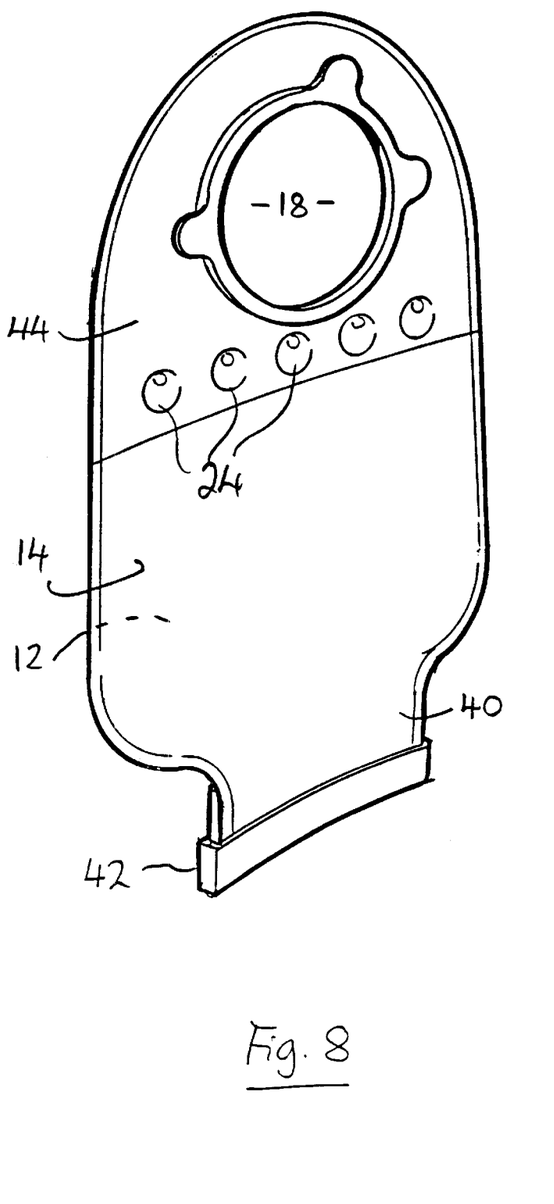
FIG. 8 is a perspective view illustrating a sixth ileostomy pouch.

FIG. 8 shows an alternative arrangement of the rupturable pockets 24 on the front wall 12 of the pouch 10. Instead of being arranged generally vertically, the pockets 24 are arranged in a horizontal row. The length of the curtain 44 behind the rupturable pockets 24 is sufficient to shield the stoma aperture 18 from direct release of concentrated agent from the rupturable pockets 24.

Figure 9:
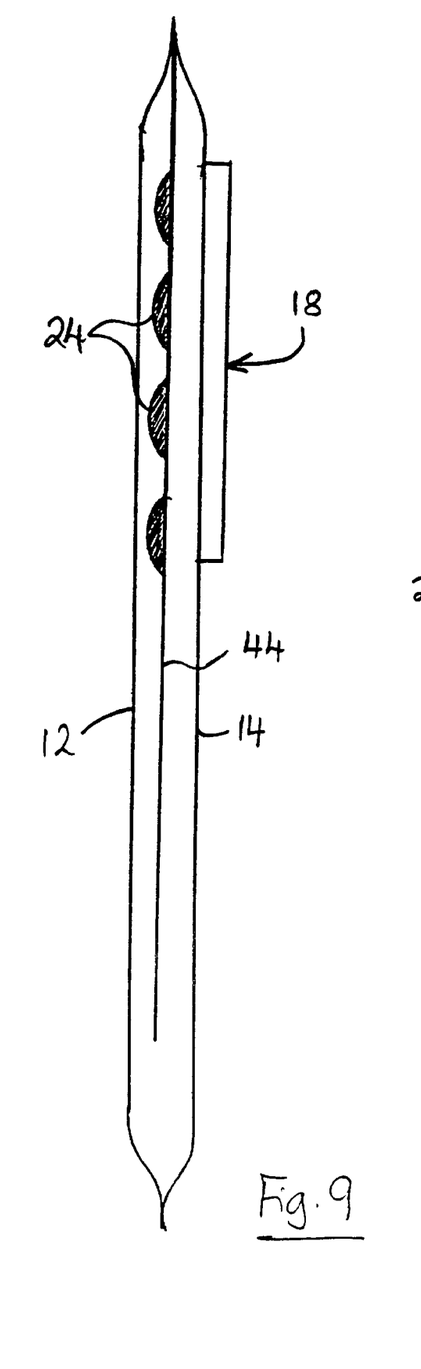
FIG. 9 is a sectional view through a seventh embodiment of ostomy pouch.

FIG. 9 illustrates a yet further embodiment of ostomy pouch including a curtain 44. However, in contrast to the previous embodiments in which the rupturable pockets 24 are carried by the front or rear wall of the pouch, in FIG. 9 the rupturable pockets 24 are carried by the curtain 44. Each pocket 24 is configured to rupture on the side of the curtain 44 facing the front wall 12. Therefore, as in the embodiment illustrated in FIGS. 7 and 8, the curtain 44 can shield the stoma aperture 18 to substantially prevent concentrated agents from spurting directly through the stoma aperture 18.

The rupturable pockets 24 are positioned on the curtain 44 so that they are not in register with the stoma aperture 18. For example the pockets 24 may be offset laterally to one, or both sides, of the aperture 18. This ensures that the ostomate will be able to rupture any desired pocket 24 simply by applying pressure at the appropriate point of the front and rear wall 12 and 14.

The construction illustrated in FIG. 9 may also provide certain manufacturing advantages in that, the rupturable pockets no longer have to be mounted directly on the front or rear wall of the pouch. The pockets 24 can be produced integrally, or sealed to a sheet for forming the curtain, which is then simply placed in register with the front and rear walls for welding. The rupturable pockets 24 are positioned to be clear of the weld seam, so there is little risk of damage to the pockets during welding of the seam 16. It will also be appreciated that the curtain 44 carrying the rupturable pockets 24 can be secured using the existing single welding process for welding around the peripheral seam 16. This can allow existing manufacturing machines and technology to be used with little, or no modification. It will also be appreciated that, if desired, the curtain 44 of any of the embodiments in FIGS. 7, 8 or 9, could be attached separately to either the front or rear wall of the pouch if, this is deemed desirable.

Figure 10:
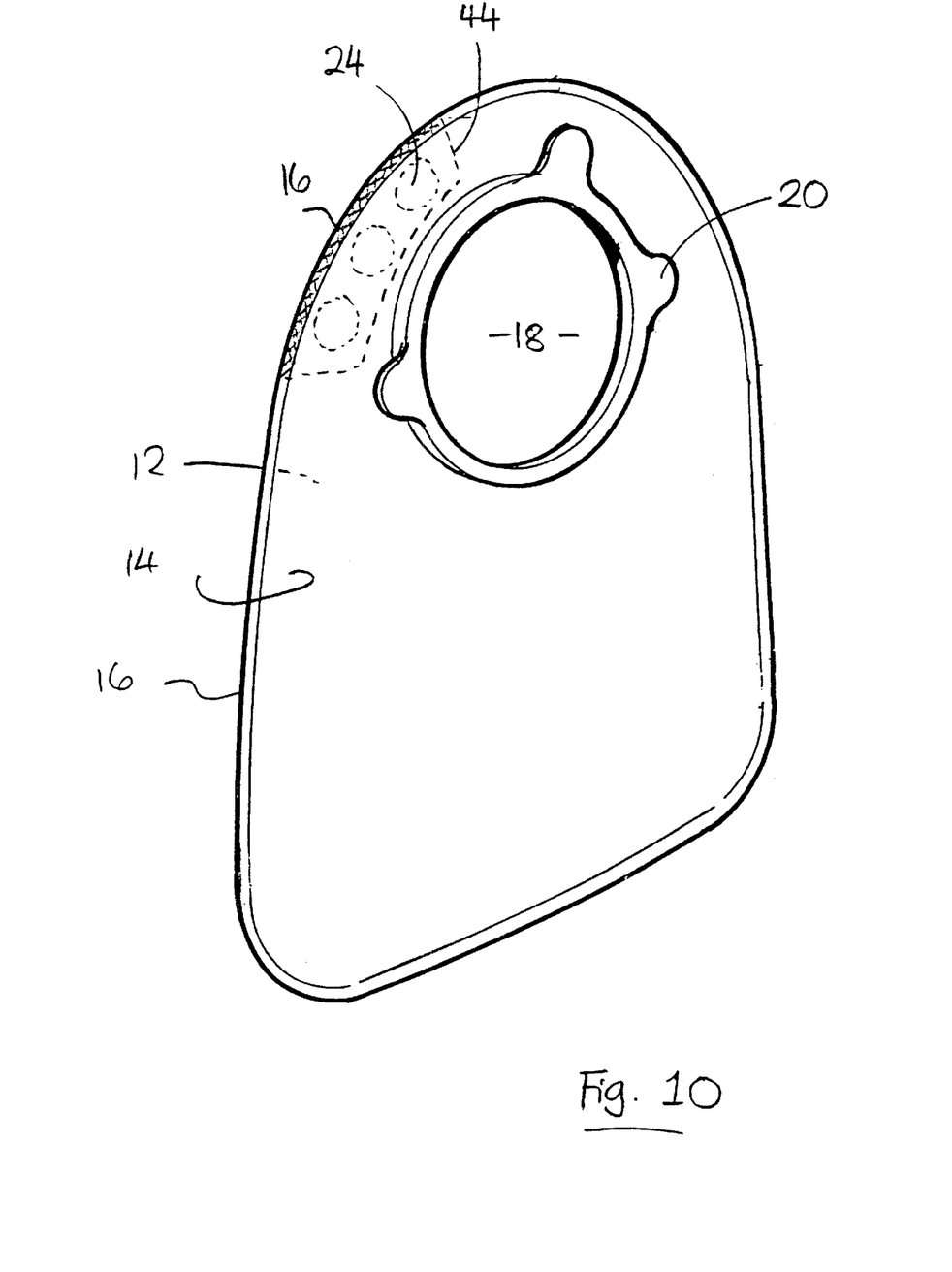
FIG. 10 is a schematic perspective view of an eighth embodiment of pouch.

FIG. 10 illustrates a modified form of pouch in which the carrier wall or curtain 44 carrying the rupturable pockets 24 extends partly around the stoma aperture, and has a curved shape so as not to obstruct the aperture. As described previously, the wall 44 is joined to both the front and rear walls 12 and 14 of the pouch at the common weld seam.

Figure 11:
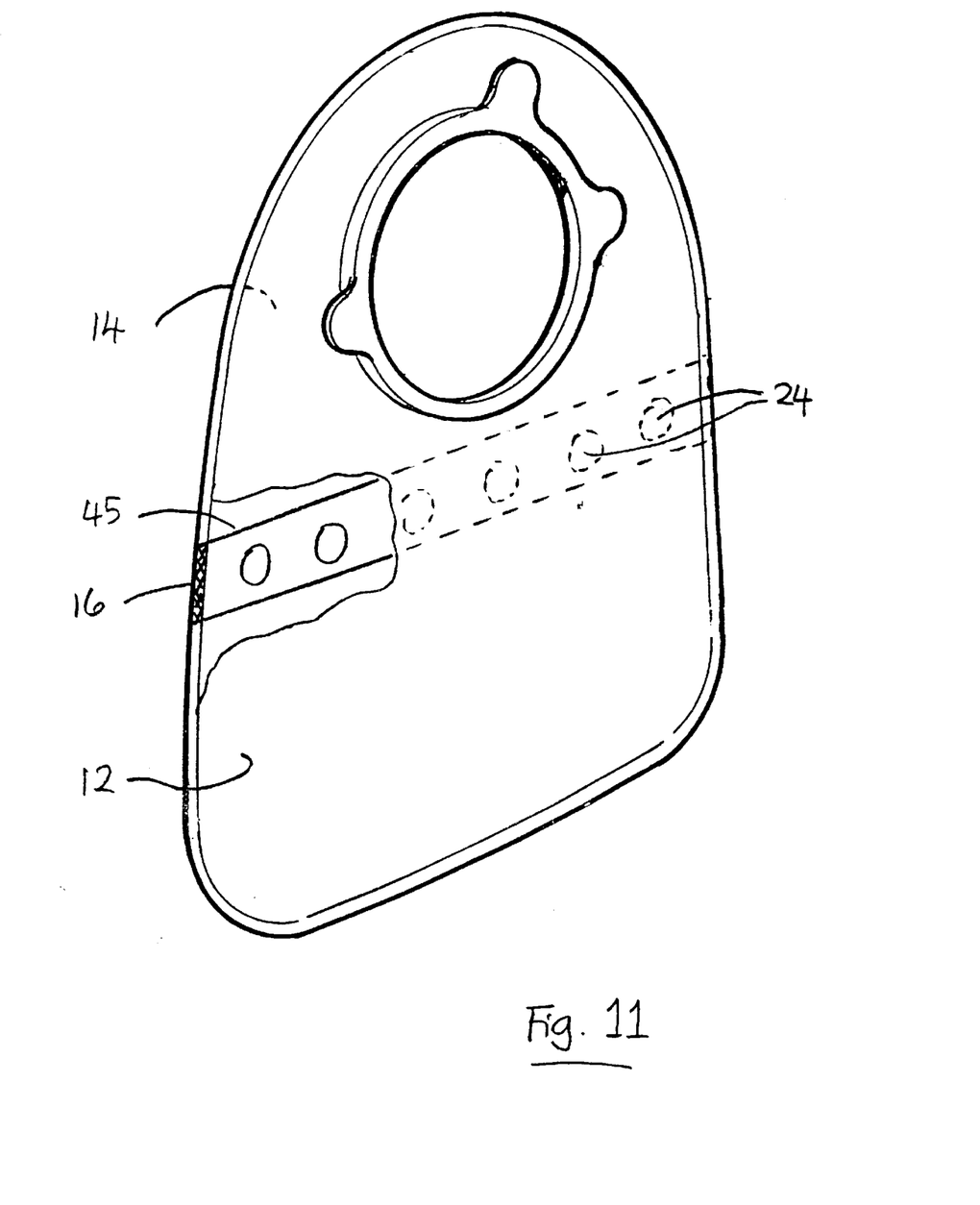
FIG. 11 is a schematic perspective view of a ninth embodiment of pouch.

FIG. 11 illustrates a further modified form of pouch in which the rupturable pockets 24 are carried by a linear tape or strip 45 which extends across the width of the pouch, (for example just below the level of the stoma aperture). The ends of the strip 45 are secured to the front and rear walls 12 and 14 at the common weld seam 16.

Figure 12:
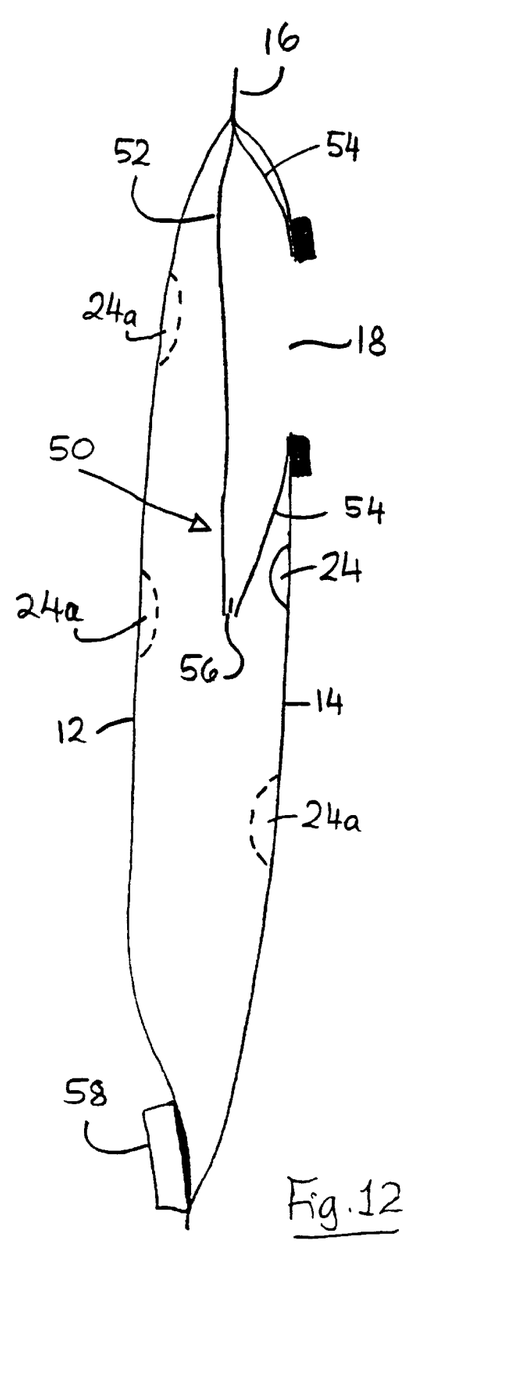
FIG. 12 is a sectional view through a tenth embodiment of a urostomy pouch.

FIG. 12 illustrates an urostomy pouch 10 carrying at least one rupturable pocket 24 containing an agent or additive for affecting the contents of the pouch. In this embodiment, the upper region of the pouch contains a one-way drip valve 50, which is formed by two plastic sheets 52 and 54 which are welded together at their top and side regions as part of the common peripheral seam 16. The lower most edges of the sheets 52 and 54 are joined together by intermittent spot welds (indicated by line 56) leaving gaps therebetween. In use, liquid entering the aperture 18 can dribble through these clearances into the main collection area of the pouch. However, liquid does not tend to splash back through the clearances, even if the pouch 10 is shaken. This prevents splashing back of the liquid contents of the pouch.

In use, the contents of the pouch can be drained through a conventional drainage tap 58 welded to the front wall 12 of the pouch, at, or towards, its lower end.

In FIG. 12 the rupturable pockets (s) 24 are mounted on the rear wall 14 of the pouch, slightly below the stoma aperture 18. It will be appreciated that the sheet 54, and the non-return effect of the structure including sheets 52 and 54, can prevent any concentrated agent or additive released from the rupturable pockets 24 from spurting through the stoma aperture 18. It will also be appreciated that the rupturable pockets could be arranged at virtually any position on the pouch walls, illustrated, for example, by the variety of positions 24a without risk of the concentrated agent or additive spurting through the stoma aperture 18.

FIGS. 13 to 18 illustrate further embodiments using a different mounting technique. Instead of the rupturable pocket being integrally mounted or welded in position, in these embodiments, the rupturable pocket is provided as a discrete capsule 60 which is trapped in position, either by welding or by a cover.

The capsule 60 may be of any suitable or convenient shape, for example, oblong, spherical or egg-shaped, and is typically made of gelatine or other easily rupturable material.

Figure 13:
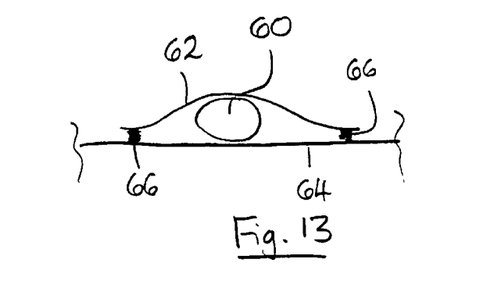
FIG. 13 is a schematic sectional view showing a further mounting technique.
Figure 15:
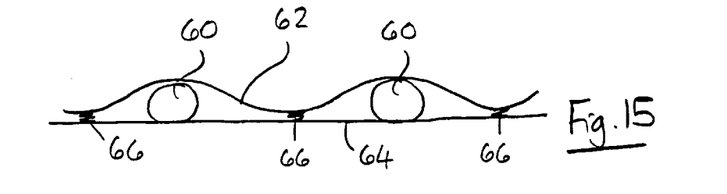
FIG. 15 is a schematic sectional view showing a modified mounting technique.
Figure 16:
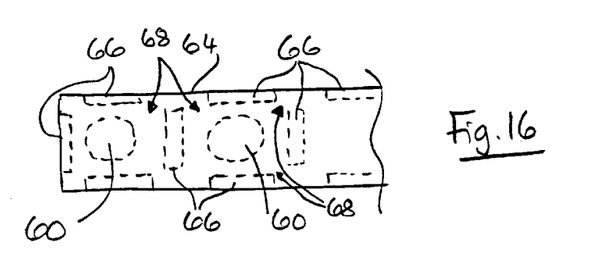
FIG. 16 is a schematic plan view of the arrangement of FIG. 15.

Referring to FIGS. 13 and 15, the capsule 60 is trapped in position by means of a cover sheet 62 welded or otherwise secured to a sheet 64 on which the capsule 60 is mounted. The mounting sheet 64 may be either the pouch front wall 12, the pouch rear wall 14, or an intermediate wall, curtain or strip 44 or 45 secured in the pouch.

The cover sheet 62 might in some embodiments be of gas permeable material, or it may be perforated or comprise one or more discharge openings to allow the contents of the capsule 60 to escape into the pouch when the capsule 60 is ruptured.

Figure 14:
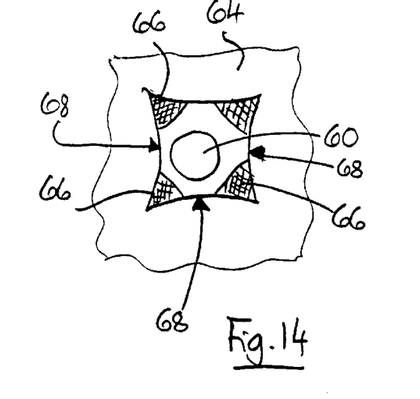
FIG. 14 is a plan view of the mounting of FIG. 13.

Additionally, or alternatively (as illustrated in FIG. 14), the cover sheet 62 may be secured to the mounting sheet 64 by discontinuous welds 66 leaving gaps 68 through which the contents of the capsule 60 can be discharged.

The mounting sheet 64 may carry a plurality of capsules 60. Each capsule may be trapped in position by its own cover sheet. Alternatively, as illustrated in FIGS. 15, a cover sheet may be provided over the plurality of capsules, and be welded at intermediate points 66 to trap each capsule in a predetermined position.

As a further modification, two or more capsules 60 could be loosely retained together in an envelope defined by the mounting sheet 64 and the cover sheet 62. Such an envelope might by more straight forward to manufacture, but might result in a less desirable product for the ostomate because the ostomate would have to find and trap a capsule while squeezing it; the capsule might tend to move to one side while being squeezed.

Figure 17:
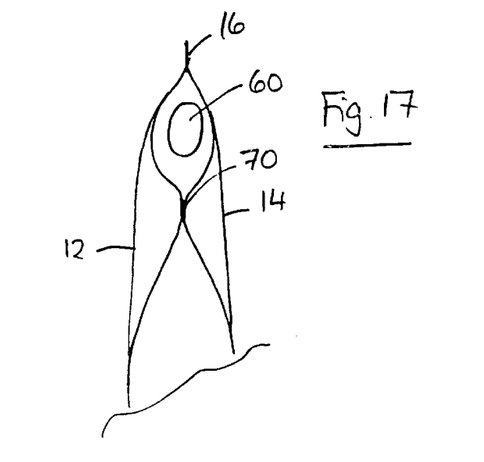
FIG. 17 is a schematic sectional view showing a further mounting technique.
Figure 18:
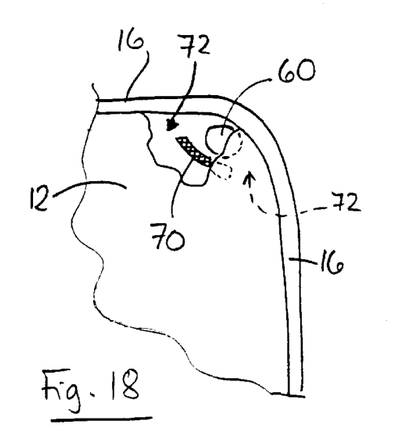
FIG. 18 is a cut away front view of the arrangement of FIG. 17.

Referring to FIGS. 17 and 18, a further mounting technique is illustrated for mounting the or each capsule 60. Instead of using a separate cover sheet 62, the capsules 60 are trapped by one or more welds 70 between the front and rear walls 12 and 14 of the pouch. One or more gaps 70 between discontinuous weld regions permit the contents of the capsule 60 to escape into the main collection region of the pouch when the capsule 60 is ruptured.

In a similar manner to that mentioned above, the welds 70 could define a plurality of regions for containing respective individual capsules of a plurality of capsules. A further possibility is that welds 70 be provided to define a larger envelope region for containing loosely a plurality of capsules 60.

As described previously, the rupturable products 24 or capsules 60 may contain any desired agent in liquid, granular powder or solid form including, for example, a malodour counteractant MCA. A wide variety of MCA materials may be used, and many different MCAs are known to the skilled man.

In the above embodiments, each rupturable pocket 24 is ruptured simply by applying pressure to the front and rear walls at the appropriate position to squeeze the pocket 24. The position of the pocket may be determined either by feel, or by being visually marked on the front and rear walls. Alternatively, one or both of the front and rear walls may be made to be at least partly transparent so that the position of the rupturable pocket can be determined visually.

Although the above embodiments relate to ostomy pouches, it will be appreciated that the same principles can be used in an incontinence pouch. In its broadest aspects, the invention contemplates all such pouches.

It will be appreciated that the forwarding prescription is merely illustrative of preferred forms of the invention, and that many modifications may be made within the scope of the invention. Although features believed to be of particular importance are defined in the appended claims, the applicant claims protection for any noel feature, or idea, described herein, and/or illustrated in the accompanying drawings, where or not emphasise has been placed thereon.

I claim:

1. An ostomy or incontinence pouch comprising a first wall and a second wall defining an envelope, and a capsule containing an agent for affecting the contents of the pouch, the capsule being captive in a capsule containing region of the pouch defined on one side by the first wall, and on the other side by plastics material secured to the first wall at one or more positions around the capsule, wherein the positions of the regions are separated by one or more gaps to allow release of the agent from said region when the capsule is ruptured.

2. A pouch according to claim 1, wherein the capsule is responsive to humidity.

3. A pouch according to claim 1, wherein the capsule is responsive to temperature.

4. A pouch according to claim 1, wherein the capsule is loose in the pouch.

5. A pouch according to claim 1, wherein the size of the or each gap is smaller than the size of the capsule at least prior to rupturing, thereby to prevent escape of the capsule.

6. A pouch according to claim 1, wherein said sheet of plastic material is a cover sheet within the pouch.

7. A pouch according to claim 6, wherein the cover sheet comprises openings and/or is of porous material.

8. A pouch according to claim 1, wherein a first capsule and a second capsule of the plurality of capsules contain respective non-identical agents.

9. An ostomy or incontinence pouch comprising a front wall, a rear wall, and a carrier located between the walls, the carrier and walls being welded together at a common weld seam, and the carrier carrying or comprising a capsule containing an agent for affecting the contents of the pouch in use, the capsule being positioned clear of the weld seam, and the agent being releasable from the capsule in use.

10. A pouch according to claim 9, wherein a least a portion of the carrier is located above a stoma aperture of the pouch.

11. A pouch according to claim 9, wherein the carrier is shaped and/or is positioned so as not the block substantially a stoma aperture of the pouch.

12. A pouch according to claim 11, wherein the carrier has a curved shape.

13. A pouch according to claim 9, wherein the carrier is in the form of a curtain.

14. A pouch according to claim 9, wherein the carrier shields a stoma aperture defined in the rear wall.

15. A pouch according to claim 9, wherein the carrier is secured at least at an uppermost portion.

16. A pouch according to claim 9, wherein the carrier is secured at least at opposite side edge regions.

17. A pouch according to claim 9, wherein a lower edge of the carrier is unsecured.

18. An ostomy or incontinence pouch comprising a front wall, and rear wall, having stoma or entrance aperture, the pouch further comprising a capsule containing an agent for affecting the pouch contents in use, and means for shielding the stoma aperture to obstruct spurting of the agent through the aperture when released from the capsule.

19. A pouch according to claim 18, wherein the shielding means comprises an intervening wall between the front and rear walls.

20. A pouch according to claim 18, wherein the intervening wall is attached to both the front and rear walls at a common weld seam.

21. A pouch according to claim 18, wherein the intervening wall is secured at least at an uppermost region.

22. A pouch according to claim 18, wherein the intervening wall is secured at least at opposite side edge regions.

23. A pouch according to claim 19, wherein a lower edge of the intervening wall is unsecured.

24. A pouch according to claim 19, wherein the intervening wall is at least coextensive with the capsule.

25. A pouch according to claim 19, wherein the capsule is located on the rear wall of the pouch.

26. An ostomy or incontinence pouch comprising first and second rupturable capsules, the first capsule containing a first agent releasable into the pouch upon squeezing the first capsule to cause the capsule to rupture, and the second capsule containing a second agent releasable into the pouch upon squeezing the second capsule to cause the capsule to rupture, the second agent being non-identical to first agent.

27. A pouch according to claim 26, wherein at least one agent comprises a deodorizing agent for absorbing, changing or masking an odor.

28. A pouch according to claim 27, wherein the deodorising agent is a fragrance.

29. A pouch according to claim 26, wherein at least one agent comprises a disinfectant.

30. A pouch according to claim 26, wherein at least one agent comprises a preservative.

* * * * *